(12) United States Patent
Shigemura

(10) Patent No.: US 9,390,337 B2
(45) Date of Patent: Jul. 12, 2016

(54) ALERTNESS LEVEL DETECTION APPARATUS AND ALERTNESS LEVEL DETECTION METHOD

(71) Applicant: DENSO CORPORATION, Kariya, Aichi-pref. (JP)

(72) Inventor: Shusaku Shigemura, Kariya (JP)

(73) Assignee: DENSO CORPORATION, Kariya, Aichi-pref. (JP)

(*) Notice: Subject to any disclaimer, the term of this patent is extended or adjusted under 35 U.S.C. 154(b) by 0 days.

(21) Appl. No.: 14/763,802

(22) PCT Filed: Jan. 16, 2014

(86) PCT No.: PCT/JP2014/000175
§ 371 (c)(1),
(2) Date: Jul. 27, 2015

(87) PCT Pub. No.: WO2014/119235
PCT Pub. Date: Aug. 7, 2014

(65) Prior Publication Data
US 2015/0363657 A1 Dec. 17, 2015

(30) Foreign Application Priority Data
Jan. 29, 2013 (JP) ................. 2013-013972

(51) Int. Cl.
*G06K 9/00* (2006.01)
*A61B 5/18* (2006.01)

(52) U.S. Cl.
CPC .............. *G06K 9/00845* (2013.01); *A61B 5/18* (2013.01); *G06K 9/00221* (2013.01)

(58) Field of Classification Search
None
See application file for complete search history.

(56) References Cited

U.S. PATENT DOCUMENTS

| 6,927,694 | B1* | 8/2005 | Smith | B60K 28/066 340/573.1 |
|---|---|---|---|---|
| 9,198,575 | B1* | 12/2015 | Blacutt | A61B 3/113 |
| 2006/0132319 | A1 | 6/2006 | Isaji et al. | |
| 2009/0097701 | A1 | 4/2009 | Nagai et al. | |
| 2010/0241021 | A1 | 9/2010 | Morikawa et al. | |
| 2013/0245886 | A1* | 9/2013 | Fung | B60K 28/06 701/36 |

FOREIGN PATENT DOCUMENTS

| JP | H09-254742 A | 9/1997 |
|---|---|---|
| JP | 2002-025000 A | 1/2002 |

(Continued)

OTHER PUBLICATIONS

International Search Report and Written Opinion (English translation); International Application No. PCT/JP2014/000175; mailed on Apr. 1, 2014.

*Primary Examiner* — Siamak Harandi
(74) *Attorney, Agent, or Firm* — Knobbe, Martens, Olson & Bear, LLP

(57) ABSTRACT

An alertness level detection apparatus, which is equipped to a vehicle and detecting alertness level of a driver, includes a stimulus information acquirer detecting stimulus applied to driver's visual sensation within driver's visual field under a state in which the driver watches in travel direction of the vehicle and acquiring stimulus information related to occurrence time and occurrence position of the stimulus within the driver's visual field, a face image generator generating a face image of the driver, a line-of-sight position detector detecting line-of-sight position of the driver by analyzing the face image, a moving time duration detector detecting moving time duration taken for the driver to move the line of sight to the occurrence position of the stimulus immediately after the occurrence time of the stimulus, and an alertness level determiner determining the alertness level of the driver based on the moving time duration.

9 Claims, 11 Drawing Sheets

(56) References Cited

FOREIGN PATENT DOCUMENTS

| | | |
|---|---|---|
| JP | 2006-158740 A | 6/2006 |
| JP | 2009-022370 A | 2/2009 |
| JP | 2010-231337 A | 10/2010 |
| JP | 2011-128799 A | 6/2011 |
| JP | 2011-206072 A | 10/2011 |
| WO | WO2014/119235 A1 | 8/2014 |

* cited by examiner

ALERTNESS LEVEL DETECTION APPARATUS AND ALERTNESS LEVEL DETECTION METHOD

CROSS REFERENCE TO RELATED APPLICATION

This application is based on Japanese Patent Application No. 2013-013972 filed on Jan. 29, 2013, the disclosure of which is incorporated herein by reference.

TECHNICAL FIELD

The present disclosure relates to a technology applied to a vehicle in order to detect alertness level of a driver.

BACKGROUND ART

A proposal has been made of a technology that monitors an alertness level of a driver of a vehicle. When a decrease in the alertness level of the driver is detected, a warning message is output to the driver for the purpose of avoiding occurrence of an accident (patent literature 1). According to the proposed technology, an image of the driver's face is analyzed in order to detect a feature manifested on the face when the alertness level has decreased, and the alertness level is estimated based on a result of the detection. Further, when the alertness level is estimated, information indicating the reliability of the alertness level is detected. This makes it possible to output an appropriate warning message to the driver.

A technology for measuring an alertness level by detecting a driver's electroencephalographic signal has been proposed (patent literature 2). The electroencephalographic signal is a signal resulting from a brain activity. Thus, when the alertness level is measured based on the electroencephalographic signal, the alertness level can be directly measured instead of indirectly estimating the alertness level by detecting a feature manifested on a face. Therefore, the alertness level is expected to be detected highly precisely with a higher reliability.

However, the method of detecting a driver's electroencephalographic signal is confronted with a problem that an instrument for detecting the electroencephalographic signal has to be attached to the driver's head. The electroencephalographic signal is a substantially feeble signal and is easy to be affected by noise. This poses a problem that it is not easy to ensure precision and reliability in detection of an alertness level of the driver.

PRIOR ART LITERATURES

Patent Literature

Patent literature 1: JP 4582137 B2
Patent literature 2: JP 4500369 B2

SUMMARY OF INVENTION

In view of the foregoing difficulties, it is an object of the present disclosure to provide an alertness level detection apparatus and an alertness level detection method each of which enables a direct detection of an alertness level of a driver at a higher accuracy and a higher reliability without attaching a special instrument for alertness level measurement to the driver.

According to a first aspect of the present disclosure, an alertness level detection apparatus, which is equipped to a vehicle and detects an alertness level of a driver, includes a stimulus information acquirer, a face image generator, a line-of-sight position detector, a moving time duration detector, and an alertness level determiner. The stimulus information acquirer detects a stimulus newly applied to a visual sensation of the driver within a viewable range of the driver under a state in which the driver watches in a travel direction of the vehicle and acquires stimulus information related to an occurrence time of the stimulus and an occurrence position of the stimulus within the viewable range of the driver. The face image generator generates a face image of the driver. The line-of-sight position detector detects a position of a line of sight of the driver by analyzing the face image. The moving time duration detector detects a moving time duration taken for the driver to move the line of sight to the occurrence position of the stimulus immediately after the occurrence time of the stimulus. The alertness level determiner determines the alertness level of the driver based on the moving time duration.

With above apparatus, the alertness level of the driver can be detected in a direct manner without attaching a special instrument for alertness level measurement to the driver. Thus, the alertness level of the driver can be detected at a higher accuracy and a higher reliability.

According to a second aspect of the present disclosure, an alertness level detection method applied to a vehicle for detecting an alertness level of a driver includes detecting a stimulus newly applied to a visual sensation of a driver within a viewable range of the driver under a state in which the driver watches in a travel direction of the vehicle, acquiring stimulus information related to an occurrence time of the stimulus and an occurrence position of the stimulus within the viewable range of the driver, generating a face image of the driver, detecting a position of a line of sight of the driver by analyzing the face image, detecting a moving time duration taken for the driver to move the line of sight to the occurrence position of the stimulus immediately after the occurrence time of the stimulus, and determining the alertness level of the driver based on the moving time duration.

With above method, the alertness level of the driver can be detected in a direct manner without attaching a special instrument for alertness level measurement to the driver. Thus, the alertness level of the driver can be detected at a higher accuracy and a higher reliability.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

Embodiments will be described below in order to clarify the present disclosure.

A. System Configuration

Figure 1:
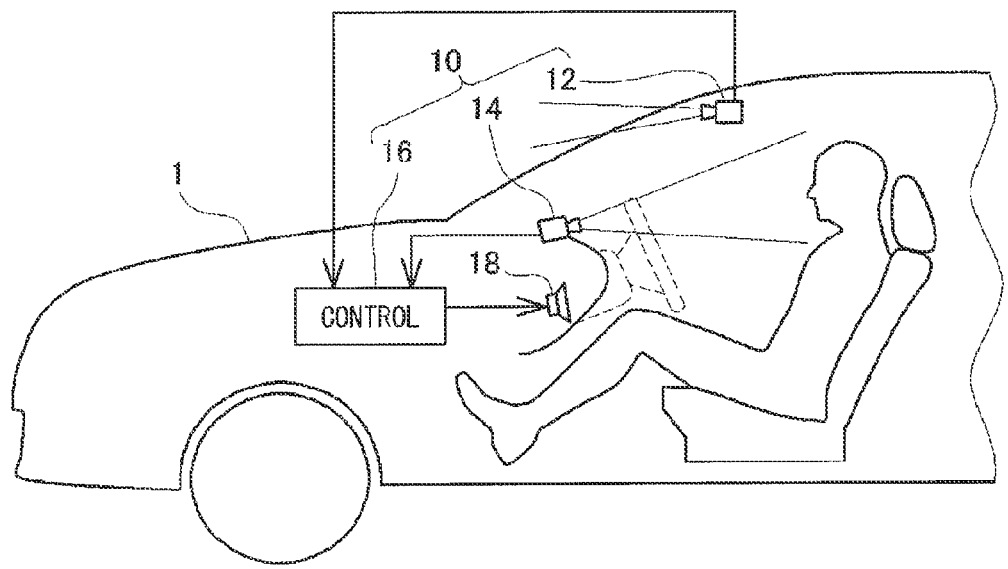
FIG. 1 is an explanatory diagram showing a vehicle equipped with an alertness level detection apparatus according to an embodiment of the present disclosure.

FIG. 1 shows an outline arrangement in a vehicle 1 equipped with an alertness level detection apparatus 10 according to the present embodiment. As illustrated, the alertness level detection apparatus 10 of the present embodiment includes a front view camera 12 that produces an image (front view image) in a travel direction of the vehicle 1, a driver camera 14 that produces an image (face image) of a face of a driver of the vehicle 1, and a control unit 16 that receives images from the front view camera 12 and the driver camera 14 respectively, and performs a process for detecting an alertness level of the driver. A speaker 18 is connected to the control unit 16. When a decrease in an alertness level of the driver is detected, the driver can be warned by a voice message or a warning sound output from the speaker 18.

The control unit 16 is provided by a microcomputer including a CPU, ROM, RAM, timer, and other components interconnected via a bus so that the CPU, ROM, RAM, timer, and other components can transmit or receive data to or from one another.

Figure 2:
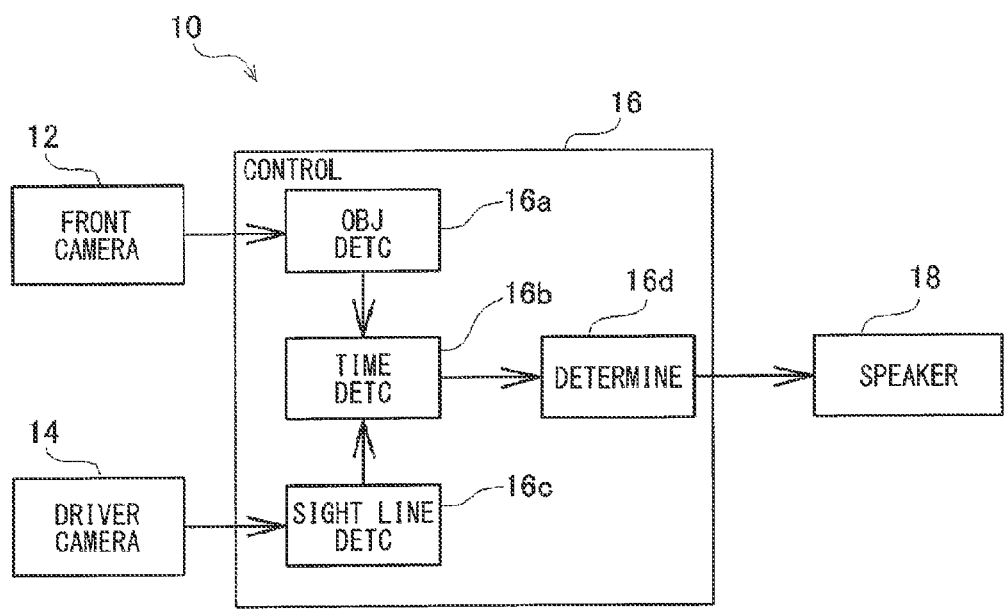
FIG. 2 is a block diagram showing a configuration of the alertness level detection apparatus according to an embodiment of the present disclosure.

FIG. 2 shows an internal configuration of the control unit 16 included in the alertness level detection apparatus 10. As illustrated, the control unit 16 (CONTROL) includes a moving object detector (OBJ DETC) 16a, a moving time duration detector (TIME DETC) 16b, a line-of-sight detector (SIGHT LINE DETC) 16c, and an alertness level determiner (DETERMINE) 16d.

Above four components of the control unit indicate the features of the control unit 16, which are classified according to a function of each component for convenience' sake. The inside structure of the control unit 16 need not be physically divided into four portions. Each of the components may be provided by hardware using an electronic circuit or CPU, or may be provided by software using a computer program or using part of a program.

On receipt of a front view image produced by the front view camera (FRONT CAMERA) 12 at regular intervals (at intervals of approximately 30 msec), the moving object detector 16a analyzes the front view image so as to detect moving objects from the front view image. Herein, the moving objects include a pedestrian, a vehicle, or the like. A pattern matching method or any other various known methods can be adopted for detecting the moving objects. When a new moving object that has not been detected from a front view image produced in the past is newly detected, information with which the timing when the new moving object is taken and the position of the new moving object can be specified and output to the moving time duration detector 16b.

The line-of-sight detector 16c analyzes the face image of the driver so as to detect a position of a driver's line of sight on receipt of a face image of the driver produced by the driver camera (DRIVER CAMERA) 14 at regular intervals (at intervals of approximately 30 msec). Then, the line-of-sight detector 16c outputs a detection result to the moving time duration detector 16b.

The moving time duration detector 16b detects a moving time duration which is taken for the driver to move the line of sight to the newly detected moving object based on the pieces of information transmitted from the moving object detector 16a and the line-of-sight detector 16c respectively.

The alert level determiner 16d determines a driver's alert level based on a record of the moving time duration detected by the moving time duration detector 16b. If the alert level has decreased, the driver is warned by a voice message or a warning sound output from the speaker (SPEAKER) 18. An action for warning the driver is not limited to outputting the voice message or the like from the speaker 18. Alternatively, the method for warning the driver may include lighting a lamp that is not shown or vibrating a steering wheel that is manipulated by the driver to steer the vehicle. Instead of warning the driver, the air-conditioning temperature of the vehicle 1 may be lowered in order to alert the driver.

In the present disclosure, the front view camera 12 corresponds to a front view image generator, and the driver camera 14 corresponds to a face image generator. In the present disclosure, the moving object detector 16a that detects moving objects from a front view image corresponds to a stimulus information acquirer, and the line-of-sight detector 16c that detects a line of sight from a face image corresponds to a line-of-sight position detector.

It is noted that a flowchart or the processing of the flowchart in the present disclosure includes sections (also referred to as steps), each of which is represented, for instance, as S100. Further, each section can be divided into several sub-sections while several sections can be combined into a single section. Furthermore, each of thus configured sections can be also referred to as a circuit, device, module, or means.

B. First Embodiment

B-1. Alertness Level Detection Process

Figure 3:
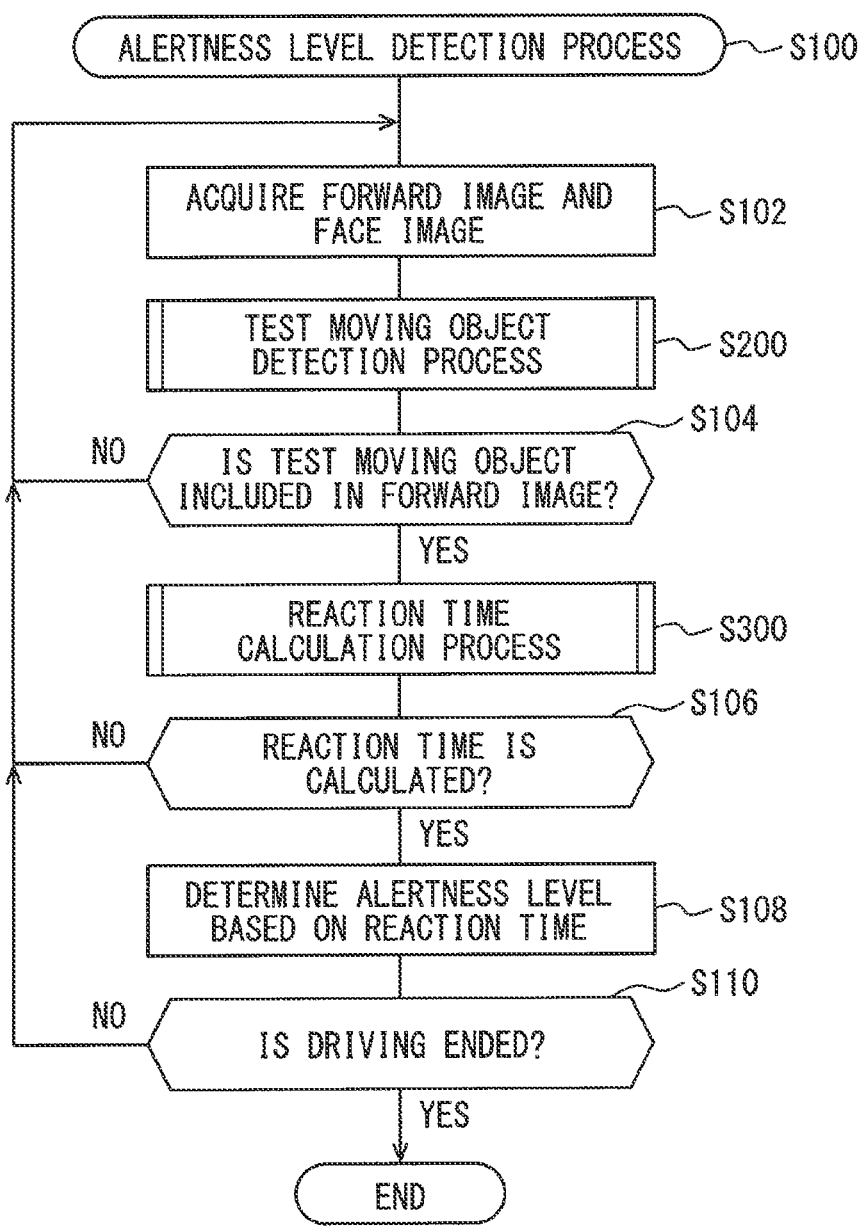
FIG. 3 is a flowchart showing an alertness level detection process according to a first embodiment of the present disclosure.

FIG. 3 is a flowchart showing an alertness level detection process according to the first embodiment. The control unit 16 executes the alertness level detection process.

When the alertness level detection process (S100) of the first embodiment is initiated, the control unit 16 acquires a front view image generated by the front view camera 12 and a face image generated by the driver camera 14 and stores in a frame memory that is not shown (S102). The frame memory is a kind of memory to be used to store images. In the present embodiment, part of the RAM incorporated in the control unit 16 may be used as the frame memory. Each of the front view camera 12 and the driver camera 14 generates images at predetermined intervals of approximately 30 msec. Every time a new image is produced, the new front view image or the new face image is stored in the frame memory.

The control unit executes a process (test moving object detection process) for detecting a test moving object by analyzing front view images and face images (S200). The test moving object is a moving object that is selected from moving objects included in the front view image in order to detect a driver's alertness level. The test moving object detection process will be described later. When a driver's line of sight moves to the moving object designated as the test moving object, the moving object is released from the designation as the test moving object. This point will be described later.

The control unit 16 determines whether a test moving object exists in a front view image (S104). In a case where the test moving object has been detected in the test moving object detection process performed immediately previously (S200), the control unit 16 determines that the test moving object exists in the front view image (S104: YES). When the control unit 16 fails to detect the test moving object in the immediately preceding test moving object detection process (S200) but the designation of the test moving object detected previously is not yet deactivated or released, the control unit 16 determines that the test moving object exists in the front view image (S104: YES).

When the control unit 16 determines that the test moving object is absent from the front view image (S104: NO), returns to S102, and acquires front view images and face images that are outputted, respectively, from the front view camera 12 and driver camera 14 at regular intervals.

When a test moving object exists in the front view image (S104: YES), the control unit 16 performs a process (reaction time calculation process) for calculating a driver's reaction time duration, which is taken for a driver to react on the test moving object, by detecting a time (moving time duration) which is taken for a driver's line of sight to move to the test moving object (S300). Herein, the reaction time duration is a processed time obtained by performing a predetermined statistical process to accumulated multiple records of the moving time durations, which are taken for multiple test moving objects. Reaction time calculation process will be described later.

The control unit 16 determines whether the reaction time duration has been calculated (S106). In order to calculate the reaction time duration as mentioned above, moving time durations of multiple test moving objects need to be accumulated. While the accumulation of moving time durations is not completed, the reaction time duration is determined not to have been calculated (S106: NO). In this case, the control unit 16 returns to S102, and acquires a front view image and a face image that are outputted from the front view camera 12 and driver camera 14, respectively, at regular intervals.

Figure 4:
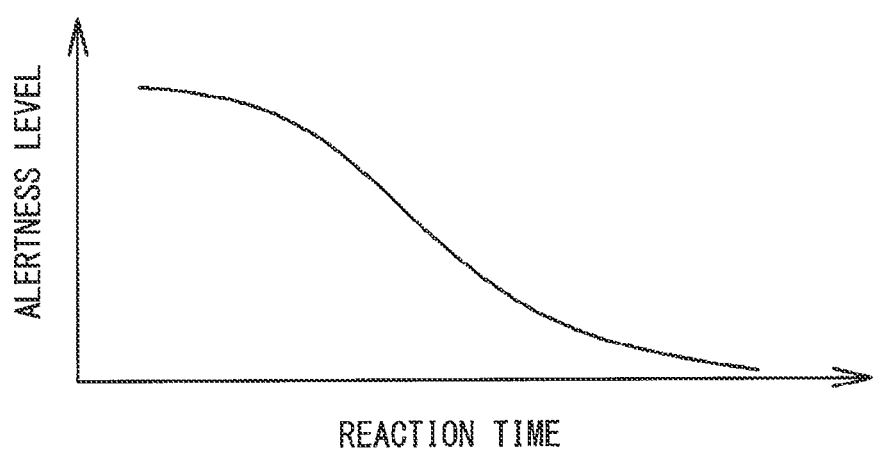
FIG. 4 is an explanatory diagram showing a correspondence relationship between a reaction time duration and alertness level.

In contrast, if a reaction time duration is determined to have been calculated (S106: YES), the control unit determines the driver's alertness level based on the obtained reaction time duration (S108). Specifically, the reaction time duration becomes shorter with an increase of the driver's alertness level, and the reaction time duration becomes longer with an decrease of the driver's alertness level. Therefore, a correspondence relationship between the alertness level and the reaction time duration like as the example shown in FIG. 4 may be obtained in advance. By referencing the correspondence relationship, the control unit 16 can determine the driver's alertness level based on the reaction time duration. The correspondence relationship shown in FIG. 4 is obtained by conducting an experiment on multiple test drivers, and stored in advance in the ROM or RAM, which is not shown, of the control unit 16.

The control unit 16 determines whether driving of the vehicle 1 is terminated is determined (S110). When driving is not terminated (S110: NO), the control unit 16 returns to S102, and acquires a front view image and a face image that are outputted from the front view camera 12 and driver camera 14, respectively, at regular intervals (S102). Then, the above-described process sequence is repeated. When the driving of the vehicle 1 is determined to be terminated (S110: YES), the control unit 16 ends the alertness level detection process shown in FIG. 3.

The following will describe the processing (test moving object detection process) for detecting a test moving object and the process (reaction time calculation process) for calculating a reaction time duration by accumulating moving time durations. As described above, the two processes are carried out in the alertness level detection process according to the first embodiment.

B-2. Test Moving Object Detection Process

Figure 5:
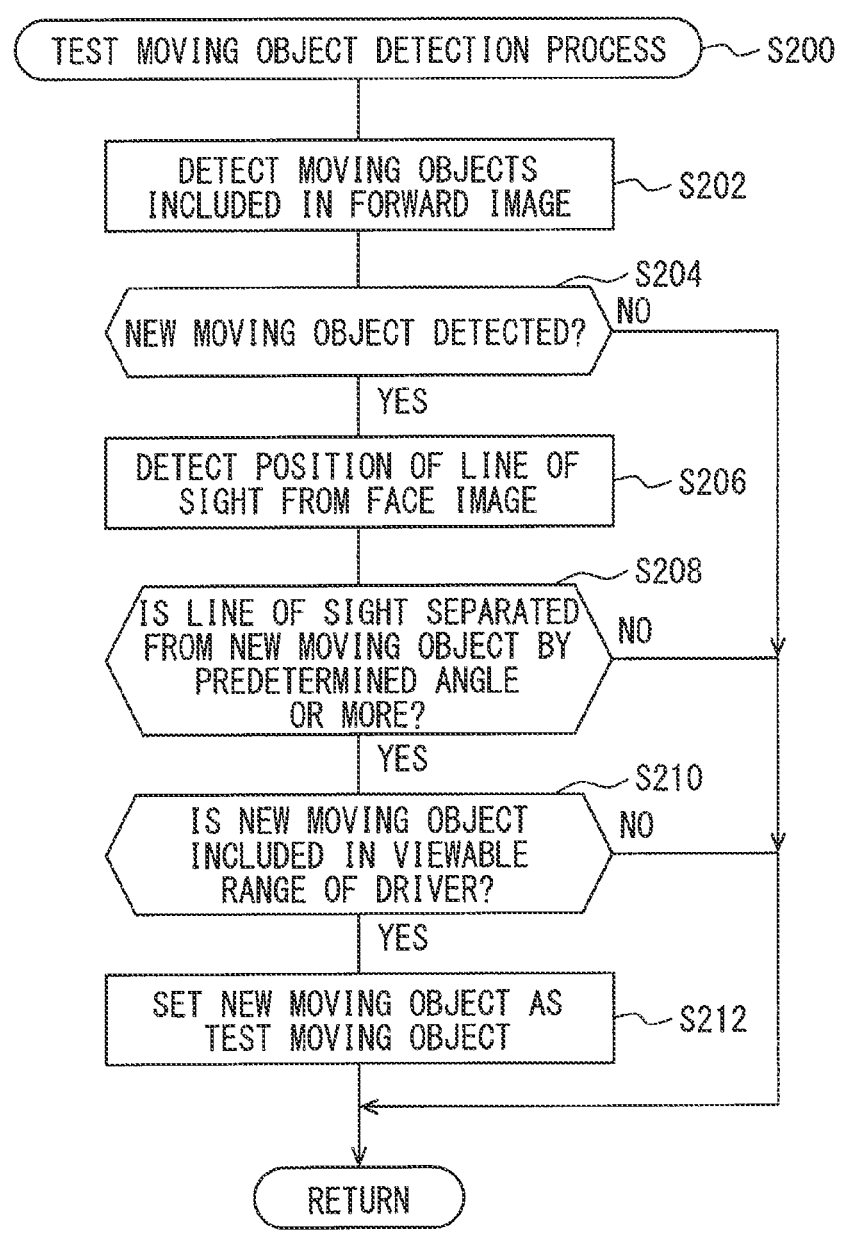
FIG. 5 is a flowchart showing a process for detecting a test moving object in the alertness level detection process.

FIG. 5 is a flowchart of a test moving object detection process to be performed in the alertness level detection process. The process is performed by the moving object detector 16a, the moving time duration detector 16b, and the line-of-sight detector 16c included in the control unit 16 shown in FIG. 2.

In the test moving object detection process (S200), first, moving objects are detected from a front view image generated by the front view camera 12 (S202). Herein, the moving objects include a pedestrian, a vehicle, a bicycle, an animal, or the like. The moving objects included in the front view image can be detected as described below.

To begin with, typical luminance change patterns observed in images of moving objects are stored in advance. Herein, the moving objects include a pedestrian, a vehicle, a bicycle, an animal or the like. Part of a front view image in which luminance is changed according to a pattern similar to any one of the typical change patterns is searched for. For example, assuming that part of a front view image exhibits a pattern similar to a change pattern of a pedestrian, the pedestrian is determined to be included in the part of the front view image. Likewise, if part of a front view image exhibits a pattern similar to a change pattern of a vehicle, the vehicle is determined to be included in the part of the front view image. If part of a front view image exhibits a pattern similar to a change pattern of an animal, the animal is determined to be included in the part of the front view image.

Naturally, a moving object located far away appears small, and a moving object located nearby appears large. Thus, a front view image is searched by varying the sizes of the typical change patterns, whereby moving objects appearing in the image are detected. Thus, moving objects having various sizes can be detected.

Thereafter, the process determines whether a new moving object has been detected (S204). Specifically, since front view images are generated at intervals of approximately 30 msec, almost all moving objects are detected in a front view image produced at a prior time point, and positions where the moving objects have been detected nearly not change. Therefore, if the same kind of moving object (pedestrian or vehicle) as a kind of moving object detected in a front view image produced this time is detected at a nearly identical position in a front view image produced previously, the moving object is determined not to be a newly detected moving object.

In contrast, when a moving object is not detected near a position, where the moving object is detected in a front view image produced this time, in a front view image produced at a prior time point, the moving object is determined to be a new moving object detected for the first time in the front view image produced this time.

When no new moving object is determined to be detected (S204: NO), test moving object detection process described in FIG. 5 is terminated without detection of a test moving object, and is returned to the alertness level detection process shown in FIG. 3.

In contrast, when a new moving object is determined to have been detected (S204: YES), a driver's face image produced by the driver camera 14 is analyzed in order to detect the position of a driver's line of sight (S206). The position of the line of sight is detected as described below. First, the eyes, nose, and mouth are detected in a face image in order to calculate the orientation of a face. Thereafter, an image of the eyes is analyzed in order to detect the positions of the pupils. Based on the orientation of the face and the positions of the pupils, the position of the driver's line of sight is detected.

After the position of a driver's line of sight is detected, the process determines whether the position of a new moving object detected at S202 is separated from the driver's line of sight at a predetermined angle or more than the predetermined angle (S208).

If the position of a new moving object is separated from the driver's line of sight by the predetermined angle or more (S208: YES), the process determines whether the new moving object is positioned within a range of a driver's viewable range (S210).

When a new moving object is separated from a driver's line of sight by the predetermined angle or more (S208: YES) and the moving object is positioned within the range of a driver's viewable range (S210: YES), the new moving object is designated as the test moving object (S212).

In contrast, when a new moving object is not separated from a driver's line of sight by the predetermined angle or more (S208: NO), or if the new moving object is not positioned within the range of a driver's viewable range (S210: NO), the moving object is not designated as the test moving object. Then, the test moving object detection process is terminated.

Figure 6A:
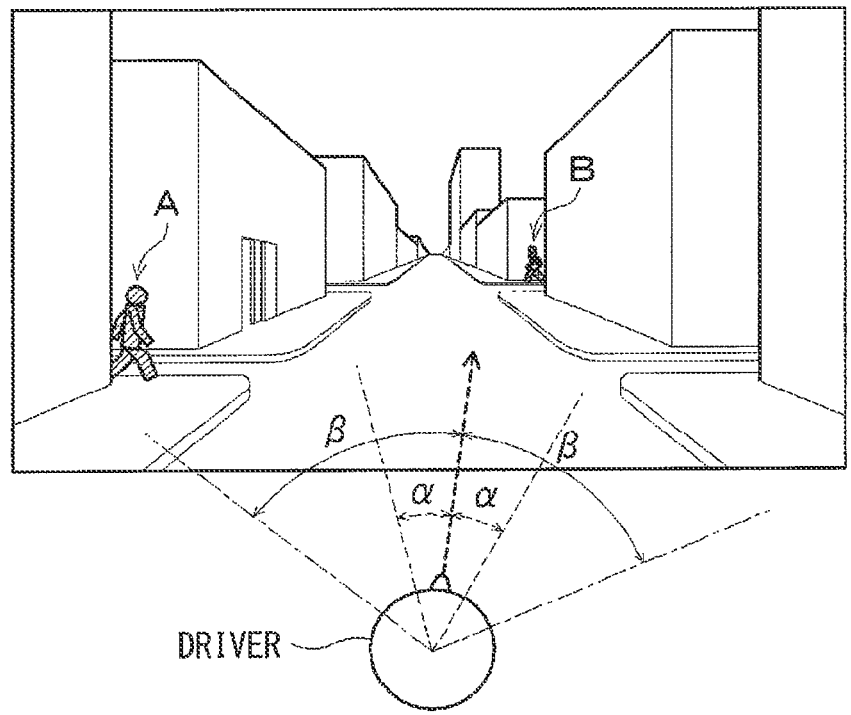
FIG. 6A and FIG. 6B are explanatory diagrams showing a method of detecting a test moving object from a front view image.
Figure 6B:
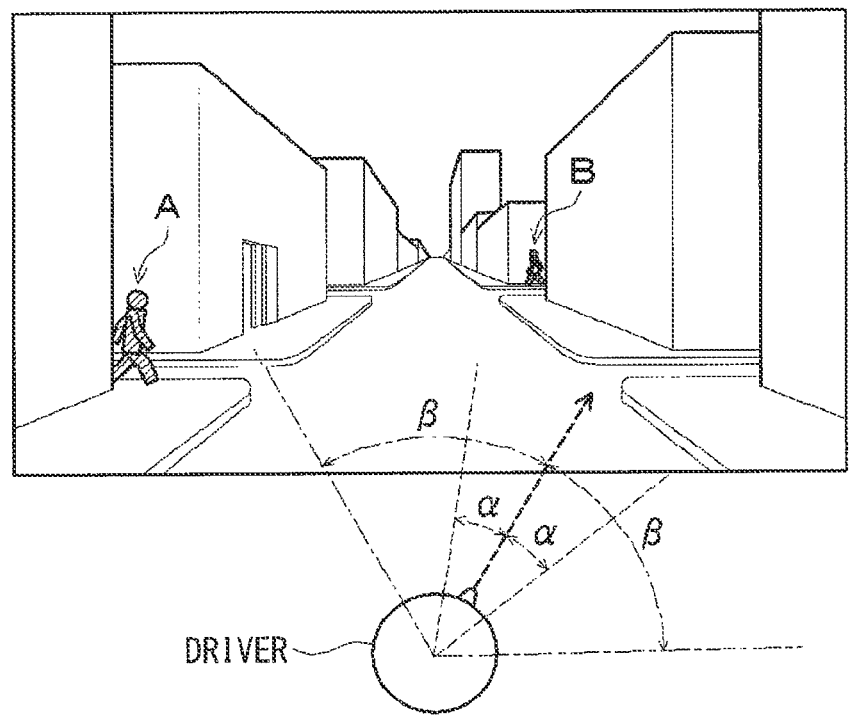

FIG. 6A and FIG. 6B show situations in which a new moving object selected in a front view image is designated as the test moving object. In the examples shown in FIG. 6A and FIG. 6B, a new pedestrian A is detected on the left side of a driver, and a new pedestrian B is detected on the forward right side of the driver. An arrow drawn with a bold dashed line in the drawing indicates a driver's line of sight. Further, an angular range covering an angle β in each of leftward and rightward directions with the driver's line of sight as a center expresses the range of a driver's viewable range.

It is quite rare that two new moving objects are, as shown in FIG. 6A and FIG. 6B, detected in one front view image. For descriptive purposes, suppose that two new moving objects of the pedestrians A and B are concurrently detected.

In the example shown in FIG. 6A, a pedestrian A on the left side of a driver is located at a position that is leftward away from the orientation of a driver's line of sight by more than a predetermined angle α. Further, the pedestrian A is positioned within the range of a driver's viewable range. Therefore, as for the new pedestrian A, YES determination is made at both S208 and S210 in FIG. 5. Thus, the pedestrian A is designated as the test moving object (S212).

In contrast, a pedestrian B on the forward right side of a driver is positioned rightward from the orientation of a driver's line of sight within the predetermined angle α. Therefore, as for the new pedestrian B, NO determination is made at S208 in FIG. 5. Thus, the pedestrian B is not designated as the test moving object.

In some cases, the driver happens to look at something else when a new moving object is detected in a front view image, and accordingly, the new moving object goes out of the range of a driver's viewable range. For example, in the example shown in FIG. 6B, the driver happens to look at an alleyway on the right side when a new pedestrian A, who is coming out of an alleyway on the left side, is detected. The pedestrian A is therefore located at a position which falls outside the range of the driver's viewable range. In this case, NO determination is made at S210 in FIG. 5. Therefore, the pedestrian A is not designated as the test moving object.

When a new moving object detected in a front view image is, as mentioned above, designated as the test moving object, the control unit 16 determines that the front view image includes the test moving object in the alertness level detection process described in FIG. 3 (S104: YES). Then, the control unit 16 starts the reaction time calculation process (S300).

In the present embodiment, when the front view camera 12 produces a front view image, the control unit 16 immediately acquires the front view image (S102 in FIG. 3), and analyzes the front view image in the test moving object detection process for detecting the moving objects. Therefore, the time point when the front view image in which the test moving object is detected has been produced is regarded equal to the time point when the test moving object is determined. Information concerning the time point when the front view image has been produced and a position in the front view image where the test moving object has been detected correspond to stimulus information in the present disclosure.

B-3. Reaction Time Calculation Process

Figure 7:
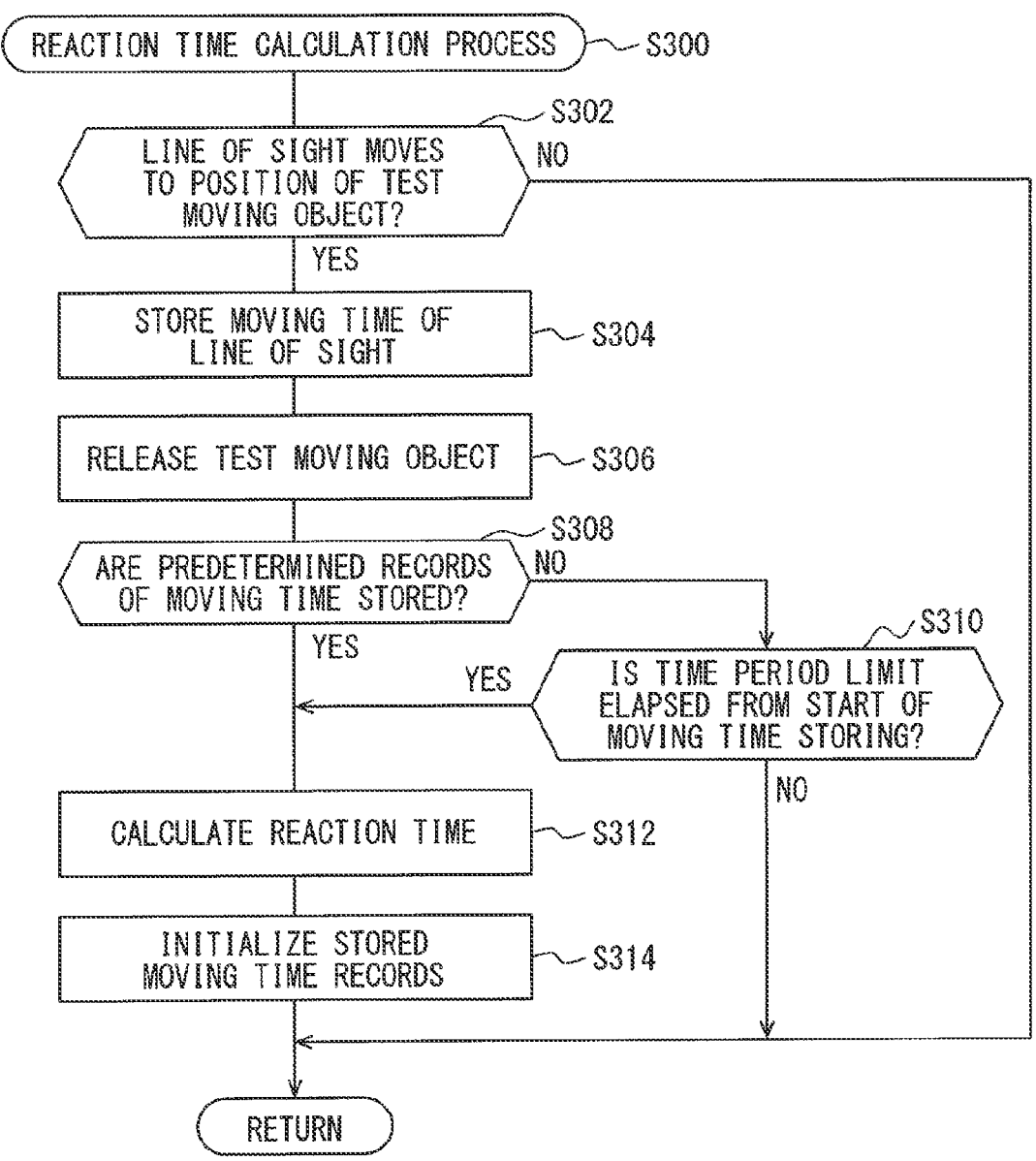
FIG. 7 is a flowchart showing a process for calculating a reaction time duration in the alertness level detection process.

FIG. 7 is a flowchart of the reaction time calculation process to be performed in the alertness level detection process. The process is performed by the alertness level determiner 16d included in the control unit 16 shown in FIG. 2.

First, the reaction time calculation process (S300) determines whether a driver's line of sight has moved to the position of the test moving object (S302). Specifically, as mentioned above, the test moving object is a newly appeared moving object that is detected within the range of a driver's viewable range when the new moving object is located away from the driver's line of sight. The moving object is an object to which the driver who is driving the vehicle 1 should pay utmost attention, such as, a pedestrian, vehicle, bicycle, or animal. Therefore, when the driver becomes aware of such a moving object (test moving object), the driver will reflectively move his/her line of sight to the test moving object. Thus, at first, the reaction time calculation process determines whether the driver's line of sight has moved to the position of the test moving object (S302).

In the process performed immediately after the test moving object is designated during the above-described test moving object detection process, the test moving object is determined to be present in a front view image (S104 in FIG. 3: YES). When the reaction time calculation process (S300) described in FIG. 7 is initiated, a driver's line of sight is not oriented to the test moving object. This is because immediately after the test moving object is designated, the test moving object (pedestrian A herein) is, as shown in FIG. 6A, located at a position away from the driver's line of sight at the predetermined angle α or more.

In this case, a driver's line of sight is determined not to have moved to the position of a test moving object (S302 in FIG. 7: NO). Reaction time calculation process described in FIG. 7 is terminated as it is without calculation of a reaction time duration, and alertness level detection process described in FIG. 3 is restored.

In the alertness level detection process after a returning from the reaction time calculation process, when determined that the reaction time duration has not been calculated (S106 in FIG. 3: NO), the process returns to the leading step of the alertness level detection process to acquire a front view image and face image from the front view camera 12 and driver camera 14 respectively (S102). As mentioned previously, the front view camera 12 and the driver camera 14 produce images at regular intervals of approximately 30 msec. Therefore, the control unit 16 acquires the front view image and the face image that are produced in approximately 30 msec after the designation of the test moving object.

The above-described test moving object detection process (S200) is performed on newly acquired front view image and the face image, and detection of moving objects is carried out to the front view image and detection of a driver's line of sight are carried out to the newly acquired face image. At this time, the possibility that an appearance and detection of a new test moving object cannot be denied. Usually, new test moving object does not frequently appear. In the present embodiment, suppose that such an event (suppose that although a previously designated test moving object remains, a new test moving object is detected in the front view image) does not take place. Namely, correct reaction time duration cannot be calculated in a situation in which multiple test moving objects are appeared in the front view image. In this case, therefore, designation of multiple test moving objects may be deactivated or released.

In the alertness level detection process after returning from the test moving object detection process, when the test moving object is determined to be exist in the front view image (S104 in FIG. 3: YES), the control unit 16 restarts the reaction time calculation process (S300) described in FIG. 7.

In the reaction time calculation process that is restarted, the control unit 16 determines whether a driver's line of sight has moved to the position of a test moving object first (S302). As described previously with reference to FIG. 6, the detected position of the test moving object away from the driver's line of sight by the predetermined angle α or more. Thus, for one set of the front view image and the face image, when the driver fails to move his or her line of sight to the test moving object, it is highly possible that the driver also fail to move his or her line of sight to the test moving object in the subsequent set of the front view image and the face image. In this case, NO determination is made at S302. Then, the reaction time calculation process described in FIG. 7 is terminated without calculation of the reaction time duration, and returns to the alertness level detection process described in FIG. 3. Thereafter, the above-described process sequence is performed on a new front view image and face image produced in next approximately 30 msec. Then, the control unit 16 determines whether the driver's line of sight has moved to the position of the test moving object again in the reaction time calculation process (S302).

Figure 8:
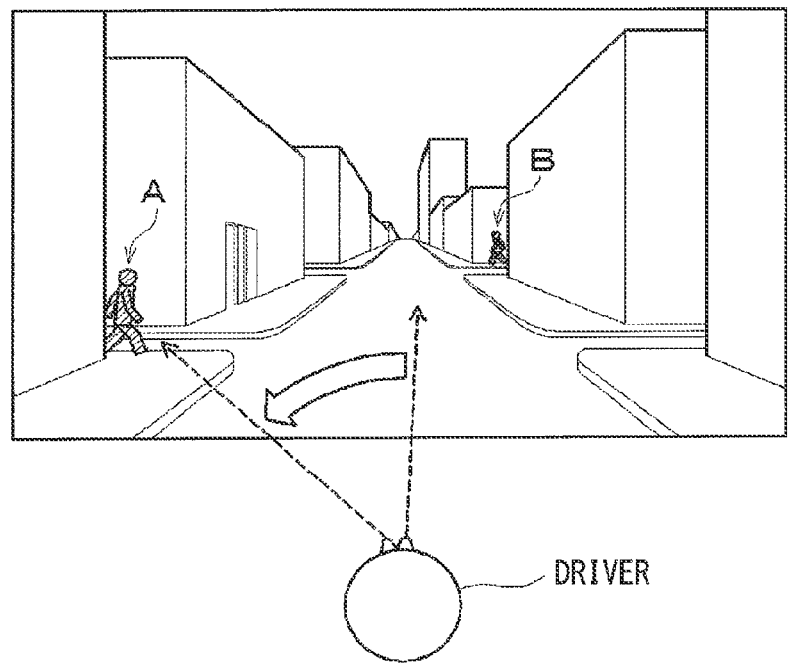
FIG. 8 is an explanatory diagram showing a situation in which a driver moves his or her line of sight to a test moving object.

During the repeated execution of the process sequence, suppose that the driver's line of sight is determined to move to the position of a test moving object (S302: YES). FIG. 8 shows a situation, in which a driver moves his/her line of sight to a pedestrian A designated as the test moving object as shown in FIG. 6A, with a blank arrow.

Then, in the reaction time calculation process, the control unit 16 stores the time (moving time duration) that is taken for the movement of the driver's line of sight to the test moving object after the test moving object has been designated (S304 in FIG. 7). For example, the control unit 16 acquires the number of times the front view images (or the face images) have been taken (the number of frames) until the driver's line of sight moves to the test moving object after the designation of the test moving object, and the number of frames is multiplied by the image taking interval (approximately 30 msec) in order to calculate the moving time duration of the line of sight to the test moving object. The obtained moving time duration is stored in a predetermined address of the RAM, which is not shown, of the control unit 16.

After the moving time duration necessary for moving the line of sight to the test moving object is stored (S304), the designation of the test moving object is released (S306). Specifically, even when a new moving object is detected in a front view image and designated as the test moving object, the new moving object is designated as the test moving object merely until a driver's line of sight moves to the moving object. Therefore, an event that multiple test moving objects are present in one front view image quite rarely takes place. That is, when the driver's line of sight moves to the test moving object and the corresponding moving time duration is stored, the designation of the moving object as the test moving object is not effective any more. Therefore, one moving time duration is stored in relation to one test moving object.

The control unit determines whether the number of the stored moving time durations has reached a predetermined number (S308). Specifically, an obtained moving time duration is thought to vary depending on at how far a position away from a driver's line of sight a test moving object is detected. If the test moving object happens to be detected in a direction in which a driver is about to move his/her line of sight, the moving time duration becomes short. Thus, there is presumably a variance among moving time durations. Therefore, a predetermined number of (for example, twenty) moving time durations is accumulated in order to restrict an adverse effect of the variance.

When the number of stored moving time durations reaches the predetermined number (S308: YES), the time (reaction time duration) taken for the driver to react on the test moving object is calculated based on the predetermined number of moving time durations (S312).

Figure 9:
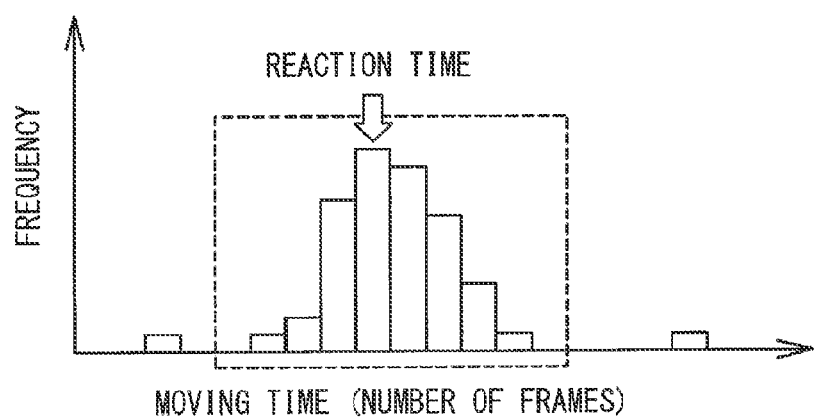
FIG. 9 is an explanatory diagram showing a method of determining a reaction time duration based on a predetermined number of moving time durations.

FIG. 9 shows a method of calculating a reaction time duration using the predetermined number of moving time durations. In FIG. 9, a frequency distribution concerning accumulated moving time durations is shown by marking the moving time durations on the axis of abscissas. In this example, the longest moving time duration and the shortest moving time duration are excluded from the accumulated moving time durations, and the reaction time duration is calculated based on the remaining moving time durations.

A reaction time duration may be obtained by calculating a mean value of the moving time durations, or a mode moving time duration having the highest frequency may be adopted as the reaction time duration. The reaction time duration may also be calculated by any other known statistical calculation. In the present embodiment, the mean value of the moving time durations is adopted as the reaction time duration so that a relatively highly precise reaction time duration can be obtained even when the predetermined number of moving time durations cannot be obtained as mentioned later.

After the obtaining of the reaction time duration (S312), all stored moving time durations are initialized (S314). Thereafter, the reaction time calculation process described in FIG. 7 is terminated, and returns to the alertness level detection process described in FIG. 3.

The accumulation of moving time durations as mentioned above and the calculation of the reaction time duration using the accumulated moving time durations are performed by the alertness level determiner 16d of the control unit 16. In the present embodiment, the alertness level determiner 16d corresponds to an accumulator and reaction time duration determiner.

When the number of moving time durations fails to reach the predetermined number of moving time durations (S308 in FIG. 7: NO), the control unit 16 determines whether an elapsed time from when storing the moving time durations is initiated has reached a predetermined time limit (S310). The reason why such a determination is made will be described below.

As mentioned above, a moving time duration indicates the time duration taken for the driver to move his/her line of sight to the test moving object. The test moving object is designated only when a moving object is newly detected within a driver's viewable range at a position away from a driver's line of sight at a predetermined angle α or more. Since the test moving object is not always frequently designated, it may take a long time to accumulate the predetermined number of moving time durations. If it takes too long time duration, there arises a possibility that a driver's alertness level may vary in the meantime. In this case, even when the predetermined number of moving time durations is used for calculating the reaction time duration, a correct reaction time duration may not be obtained.

In the present embodiment, an appropriate time limit is defined in advance. When an elapsed time since accumulation of the moving time durations is initiated reaches the time limit, even if the number of moving time durations does not reach the predetermined number of moving time durations, the moving time durations accumulated so far are used to calculate the reaction time duration.

Regarding above-described reason, in the reaction time calculation process according to the present embodiment, the control unit determines whether the elapsed time from a start of storing the moving time durations has reached a predetermined time limit (S310). The time limit is typically set to about five minutes.

When the elapsed time that is counted has not reached to the time limit (S310: NO), the reaction time calculation process described in FIG. 7 is terminated without calculating the reaction time duration, and returns to the alertness level detection process described in FIG. 3. As mentioned above, in the alertness level detection process, when the reaction time duration is determined not to have been calculated (S106: NO), the control unit returns to the leading step and acquires new front view image and new face image (S102). Thereafter, accumulation of the moving time durations is continued.

When the number of accumulated moving time durations has not reached the predetermined number (S308 in FIG. 7: NO) and the time limit is determined to have elapsed since the start of accumulation of the moving time durations (S310: YES), the accumulated moving time durations are used to calculate the reaction time duration (S312). Then, all the accumulated moving time durations are initialized (S314), and the reaction time calculation process described in FIG. 7 is terminated, and returns to the alertness level detection process described in FIG. 3.

As mentioned above, when returning to the alertness level detection process described in FIG. 3 from reaction time calculation process with the obtained reaction time duration, the control unit determines that the reaction time duration is determined to be calculated (S106: YES). As a result, as mentioned with reference to FIG. 4, the alertness level is determined by reading out the alertness level associated with a reaction speed (S108).

In the alertness level detection process according to the first embodiment, a driver's alertness level is detected based on the moving time durations which are taken for a driver to move his/her line of sight to respective test moving objects. As mentioned above, the test moving objects may include a pedestrian, vehicle, and other objects to which the driver who is driving the vehicle 1 should pay the highest attention. When the driver becomes aware of such a test moving object, the driver reflectively moves his/her line of sight to the test moving object. Therefore, a moving time duration for a certain test moving object largely depends on the time duration which is taken for the driver to become aware of appearance of the moving object or the time which is taken for the driver to move his/her line of sight reflectively. The time durations can be thought to directly reflect the quickness in a driver's brain activity. Therefore, using the moving time durations for respective test moving objects, the driver's alertness level can be detected according to a direct method.

In order to detect the moving time duration, a moving object needs to be detected in a front view image, and the position of a driver's line of sight needs to be detected in a face image. Thus, the driver may be free from wearing a special instrument for measuring the reaction time.

In addition, a technology for detecting a moving object in a front view image and a technology for detecting the position of a driver's line of sight in a face image are technologies which are widely prevailing nowadays and have their detecting precision and reliability fully established. Therefore, while the quickness in a driver's brain activity can be directly detected, unlike when an electroencephalographic signal is detected, detecting precision will not be degraded due to an adverse effect of noise, and reliability in a result of detection will not be degraded.

Further, in the present embodiment, a moving object located within the range of a driver's viewable range at a position away from a driver's line of sight is designated as the test moving object. This configuration can restrict a case that a moving object located near a position at which a driver happens to look is designated as a test moving object, and may also restrict detection of an extremely short moving time duration.

Further, since multiple moving time durations are accumulated and a driver's alertness level is detected using multiple moving time durations, the driver's alertness level can be detected highly precisely with a higher reliability.

C. Second Embodiment

In the above-described first embodiment, a correspondence relationship (see FIG. 4) between the reaction time durations and the alertness levels is obtained by conducting an experiment in which multiple test drivers are employed, and an alertness level is determined based on a reaction time duration by referencing the correspondence relationship. In this method, the alertness level is determined under an assumption that the correspondence relationship between reaction time durations and alertness levels obtained using a limited number of test drivers is established even among drivers other than the test drivers.

What will be described below makes it possible to determine an alertness level based on reaction time duration without making the foregoing assumption.

Figure 10:
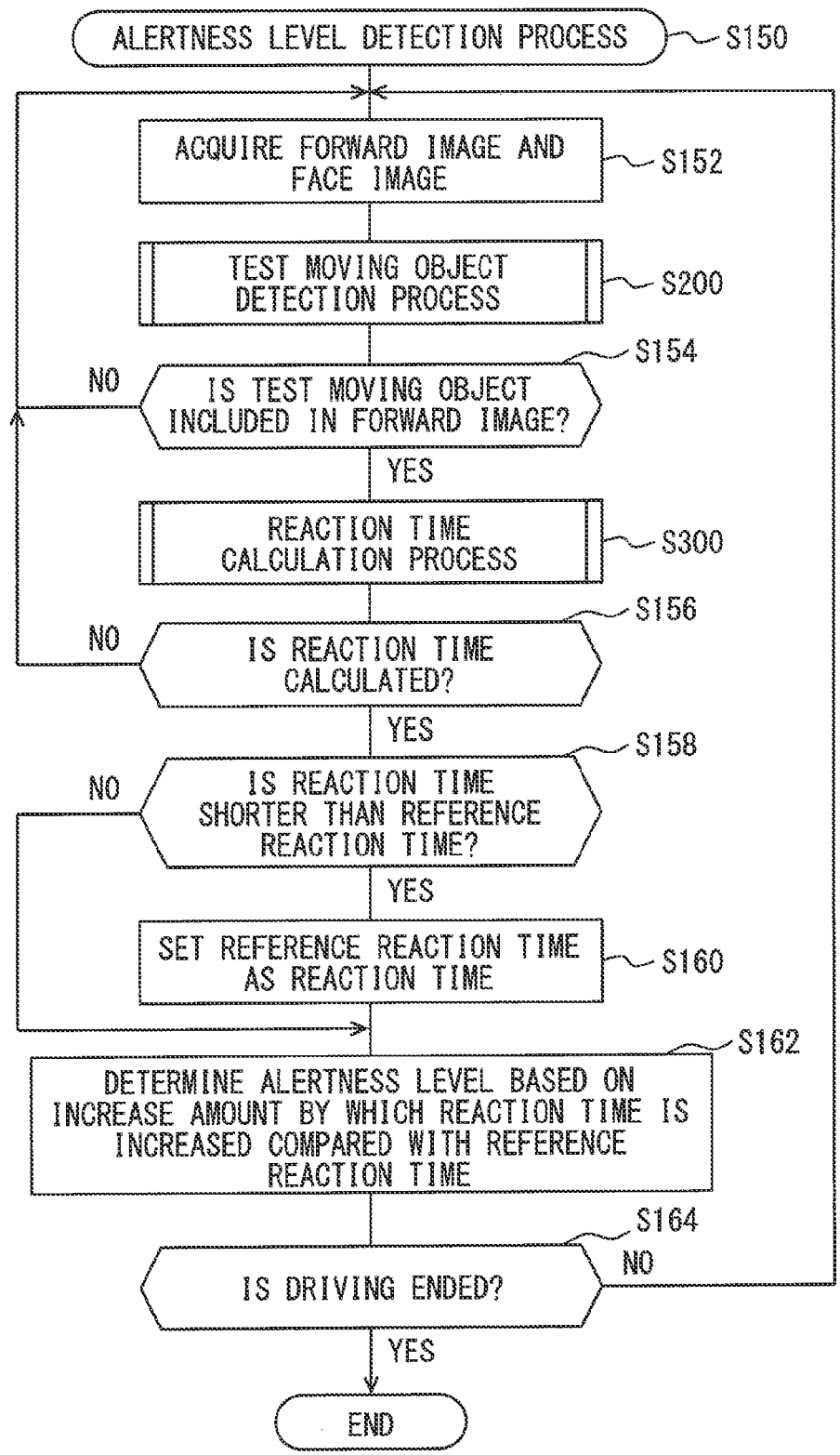
FIG. 10 is a flowchart showing an alertness level detection process according to a second embodiment of the present disclosure.

FIG. 10 is a flowchart of alertness level detection process according to a second embodiment. Alertness level detection process of the second embodiment is largely different from alertness level detection process of the first embodiment, which is described with reference to FIG. 3, in a point that an alertness level is determined based on an increase amount of the reaction time duration. The alertness level detection process of the second embodiment will be briefed below while being centered on the difference.

Even in alertness level detection process (S150) of the second embodiment, first, the control unit acquires a front view image produced by the front view camera 12 and a face image produced by the driver camera 14 and stores the images in the frame memory that is not shown (S152).

Then, the control unit detects the test moving object (test moving object detection process) by analyzing the front view image and the face image (S200). The test moving object detection process is identical to the process performed in the above-described alertness level detection process of the first embodiment. An iterative description will be omitted.

Then, the control unit determines whether the test moving object is included in the front view image (S154). As a result, when the test moving object does not exist in the front view image (S154: NO), the control unit returns to the leading step, and acquires a new front view image and a new face image that are outputted at regular intervals from the front view camera 12 and driver camera 14, respectively (S152).

When the control unit determines that the test moving object is included in the front view image (S154: YES), the control unit starts the reaction time calculation process (S300). The reaction time calculation process is identical to the process performed in the above-described alertness level detection process of the first embodiment. An iterative description will be omitted.

Then, the control unit determines whether a reaction time duration has been calculated (S156). As a result, when the reaction time duration has not been calculated (S156: NO), the control unit returns to the leading step of alertness level detection process of the second embodiment, and acquires a new front view image and a new face image to outputted at regular intervals from the front view camera 12 and driver camera 14, respectively (S152).

When a reaction time duration has been calculated (S156: YES), the control unit performs the process described below in alertness level detection process of the second embodiment.

To begin with, the control unit determines whether the reaction time duration is shorter than a reference reaction time duration (S158). The reference reaction time duration is a time duration used as a reference when determining a driver's alertness level. In the ROM, which is not shown, of the control unit 16 of the second embodiment, a reaction time duration that is a bit longer than a standard reaction time duration of an ordinary driver is stored in advance as the reference reaction time duration. When the driver starts the driving of the vehicle 1, the preliminarily stored reaction time is read out and set as an initial value of the reference reaction time duration.

When a calculated reaction time duration is shorter than the reference reaction time duration (S158: YES), the reference reaction time duration is replaced with the calculated reaction time duration (S160). For example, when a driver has good reflexes, the calculated reaction time duration may be shorter than an initial value of the reference reaction time duration. Thus, the reference reaction time duration replaced with the calculated reaction time duration. Suppose that a driver is not fully alerted immediately after he/she begins driving, but the driver gradually becomes alerted during the driving, the calculated reaction time duration may gradually become shorter. Therefore, the reference reaction time duration is replaced with the new reaction time duration every time when the new reaction time duration is calculated.

When a calculated reaction time duration is longer than the reference reaction time duration (S158: NO), the reference reaction time duration will not be replaced by the calculated reaction time duration.

When an ordinary driver or a driver having good reflexes begins driving while being fully alerted, a reference reaction time duration set to an initial value is replaced with a reaction time duration calculated first after the start of driving. Thereafter, as an alertness level decreases due to continuation of driving, the calculated reaction time duration presumably increase to get longer than the reference reaction time duration.

In a case where a driver begins driving while not being fully alerted but the driver gradually gets alerted during the driving, the reference reaction time duration will not be replaced for some time after the start of driving. As the driver gets alerted, the reference reaction time duration is replaced with a shorter reaction time duration. After the driver is fully alerted, the reference reaction time duration will not be replaced any more. Thereafter, as the alertness level decreases due to continuation of driving, the reaction time duration to be calculated will presumably increase to get longer than the reference reaction time duration.

The alertness level determiner 16d replaces the reference reaction time duration with calculated reaction time duration in case the calculated reaction time duration is shorter than the reference reaction time duration. Therefore, in the present disclosure, the alertness level determiner 16d included in the second embodiment corresponds to an updater.

In the alertness level detection process of the second embodiment, once the reaction time duration has been calculated (S158: YES), an increase amount with respect to a reference reaction time duration is calculated, and an alertness level is determined based on the increase amount (S162). Specifically, if the increase amount of the reaction time duration with respect to the reference reaction time duration is small, a driver is determined to be still in a high alertness-level state. In contrast, when the increase amount of the reaction time duration with respect to the reference reaction time duration gets larger, the alertness level of the driver is determined to being decreased.

Figure 11A:
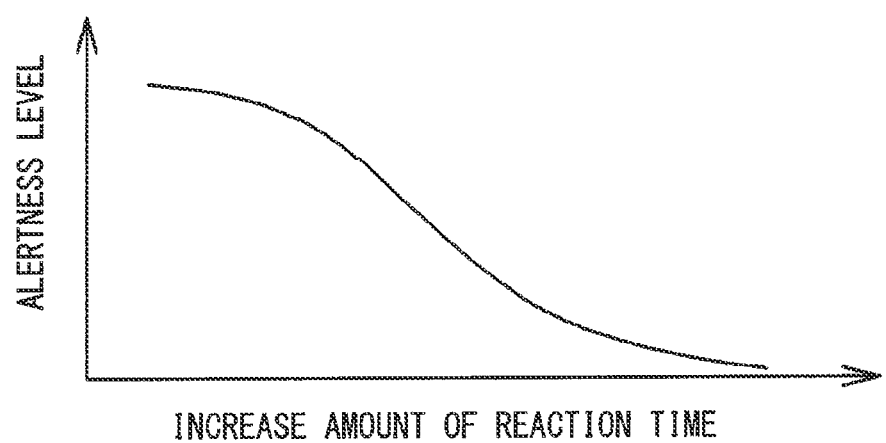
FIG. 11A and FIG. 11B are explanatory diagrams showing a correspondence relationship between an alertness level and an increase amount of a reaction time duration with respect to a reference reaction time duration.

In the alertness level detection process of the second embodiment, since the alertness levels associated with respective increase amounts regarding one reaction time duration are, as shown in FIG. 11A, designated in advance, a driver's alertness level is determined by referencing the correspondence relationship. The absolute length of the reaction time duration (reference reaction time duration) to be observed when a driver is most alerted may largely vary depending on the driver. As far as the increase amount with respective to the reference reaction time duration is concerned, a variation dependent on a driver is thought to be smaller than that of the absolute reference reaction time duration. Therefore, when an alertness level is determined based on the increase amount of the reaction time duration from the reference reaction time duration, the alertness level can be determined highly precisely without an adverse effect of the variation dependent on a driver.

Figure 11B:
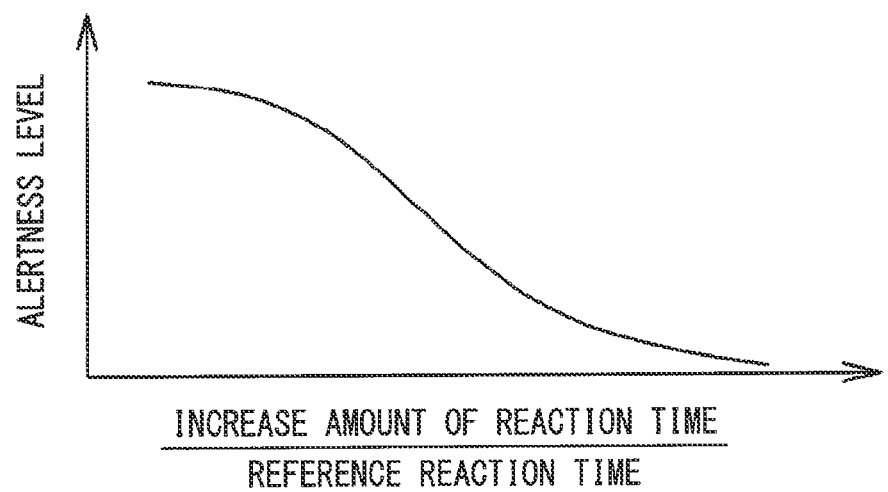

As shown in FIG. 11B, increases amount in the reaction time duration may be normalized by reference reaction time duration, and alertness levels may be stored in association with the normalized increases. In this way, although drivers are largely different from one another in the reference reaction time duration, alertness levels of the drivers can be determined using the same reference.

The correspondence relationship shown in FIG. 11A or FIG. 11B is stored in advance in the ROM or RAM, which is not shown, of the control unit 16.

The control unit determines whether the driving of the vehicle 1 is terminated (S164 in FIG. 10). When the driving is not terminated (S164: NO), the control unit returns to the leading step, and acquires a front view image and a face image outputted at regular intervals from the front view camera 12 and driver camera 14, respectively (S152). Thereafter, the above-described process sequence is repeatedly executed. If the driving of the vehicle 1 is determined to be terminated (S164: YES), the control unit ends the alertness level detection process of the second embodiment shown in FIG. 10.

In the above-described alertness level detection process of the second embodiment, a driver's alertness level is determined based on an increase amount of a reaction time duration with respect to a reference reaction time duration. Further, the reaction time duration actually measured on a driver is reflected on the reference reaction time duration. Therefore, an adverse effect of a variance in reflexes among drivers can be suppressed. Eventually, an alertness level can be detected at a higher accuracy.

In the above-described second embodiment, every time when the driving of the vehicle 1 is begun, the reference reaction time duration is updated. Therefore, even when the same driver is concerned, the reference reaction time duration varies is designated depending on the physical condition of the driver on that day.

A driver may be identified using a face image produced by the driver camera 14, and a reference reaction time duration may be stored for each driver in the RAM, which is not shown, of the control unit 16. When driving the vehicle 1 is begun, the driver may be identified using the face image produced by the driver camera 14, and a reference reaction time duration associated with the driver may be identified. In this way, even when a driver beings driving the vehicle 1 in a state in which the driver has a poor physical condition and therefore exhibits a low alertness level, the driver's alertness level can be highly precisely detected.

Further, when newly calculated reaction time duration is shorter than reference reaction time duration stored in association with a corresponding driver, stored reference reaction time duration may be changed to the newly calculated reaction time duration. In this way, during a repeated driving of the vehicle, the reference reaction time duration is updated to more correct time duration. Thus, a driver's alertness level can be detected at a higher accuracy.

D. Third Embodiment

In the above-described first and second embodiments, the apparatus detects a driver's alertness level by detecting a test moving object included in a front view image produced by the front view camera 12.

Alternatively, any stimulus can be provided to stimulate a driver's visual sensation at a position away from a driver's line of sight by a predetermined angle α or more. In this case, there is no need to set the test moving object. For example, a display device capable of performing a display (stimulus display), which stimulates the driver's visual sensation, may be mounted on a hood or the like of the vehicle 1. A driver's alertness level may be detected by using the display device that provides the stimulus to the driver, instead of detecting a test moving object in a front view image.

Figure 12:
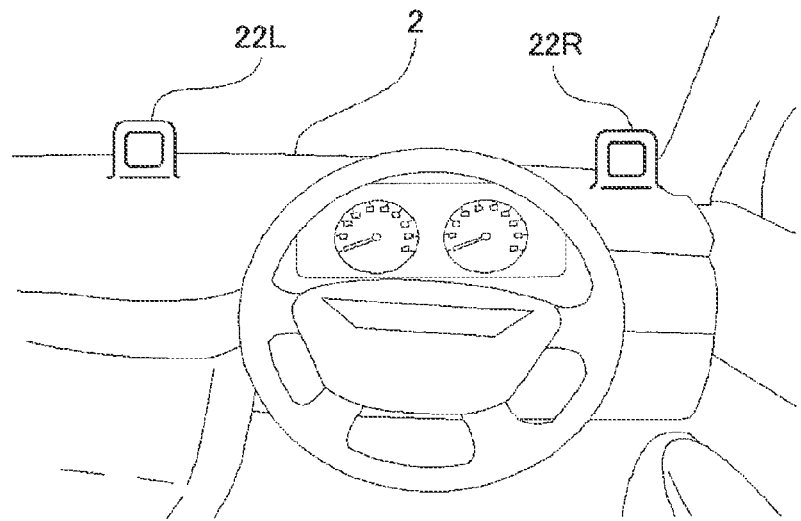
FIG. 12 is an explanatory diagram showing display devices that are disposed on a dashboard of a vehicle in order to generate stimulus display.

FIG. 12 shows display devices 22L and 22R mounted on a dashboard 2 of the vehicle 1 within a range of a driver's viewable range, and the display devices 22L and 22R provide stimulus display to stimulate a driver's visual sensation. In the shown example, the display devices 22L and 22R are arranged on left side and right side, respectively, with respect to a driver. Alternatively, one display device or three or more display devices may be mounted instead of the two display devices.

Each of the display devices 22L and 22R includes an embedded lamp. The lamp is in off state in normal state. When the lamp is turned on, a red square image can be displayed as the stimulus display. Instead of displaying the red image by turning on the lamp, the lamp itself may be displayed to a driver in order to provide the stimulus display.

Figure 13:
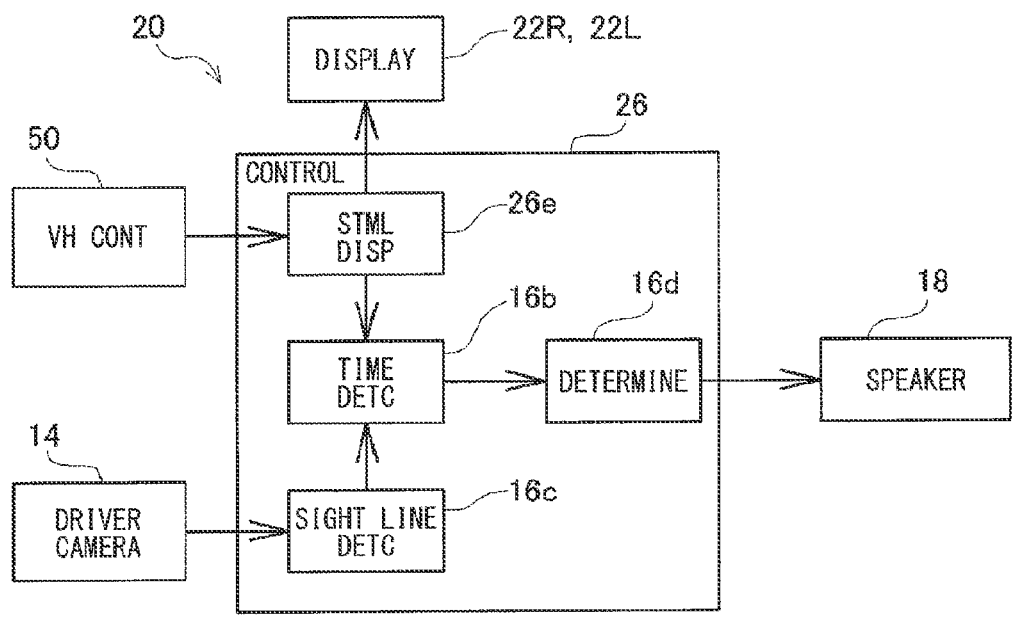
FIG. 13 is a block diagram showing a configuration of a control unit included in an alertness level detection apparatus according to a third embodiment of the present disclosure.

FIG. 13 shows an internal configuration of a control unit 26 included in the alertness level detection apparatus 20 according to the third embodiment. As shown in the drawing, compared with the control unit 16 according to the first embodiment shown in FIG. 2, the control unit (CONTROL) 26 according to the third embodiment includes a stimulus display unit 26e (STML DISP) instead of the moving object detector 16a. The display devices (DISPLAY) 22L and 22R shown in FIG. 12 are connected to the stimulus display unit 26e. A vehicle control unit (VH CONT) 50 that controls the operation of the entire vehicle 1 is connected to the stimulus display unit 26e.

In the alertness level detection apparatus 20 according to the third embodiment, information concerning the vehicle speed of the vehicle 1 and an operating state of a brake is outputted from the vehicle control unit 50 to the stimulus display unit 26e. When the vehicle 1 is in a stationary state and a depression on the brake pedal is detected, the stimulus display unit 26e turns on at least one of the left or right display device 22L, 22R for a certain period of time (for example, two sec) at random timing for performing stimulus display to a driver's visual sensation. At this time, information indicating which one of the left and right display devices 22L and 22R has been turned on is outputted from the stimulus display unit 26e to the moving time duration detector 16b.

In the third embodiment, the line-of-sight detector 16c receives a face image of a driver, which is produced at regular intervals (at intervals of approximate 30 msec) by the driver camera 14, detects the position of a driver's line of sight, and outputs a result of the detection to the moving time duration detector 16b.

On receipt of the information indicating that the display device 22L or 22R is turned on from the stimulus display unit 26e, the moving time duration detector 16b detects a moving time duration that is taken until the position of a line of sight, which is detected by the line-of-sight detector 16c, moves to the display device 22L or 22R that is turned on.

The subsequent processes are identical to the above-described processes of the control unit 16 included in the first embodiment. Specifically, the alertness level determiner 16d determines a driver's alertness level based on moving time duration detected by the moving time duration detector 16b. When the alertness level has decreased, warning message or warning sound is outputted from the speaker 18 in order to give a warning to the driver.

The stimulus display unit 26e included in the third embodiment performs stimulus display using the display devices 22L or 22R. In addition, since the stimulus display unit 26e detects a stationary state of the vehicle based on information transmitted from the vehicle control unit 50. Thus, in the present disclosure, the stimulus display unit 26e corresponds to a stationary state detector.

According to the above-described alertness level detection apparatus 20 of the third embodiment, at least one of the display devices 22L or 22R is turned on in order to perform stimulus display that stimulates a driver's visual sensation. Therefore, in the nighttime or early morning or in a situation in which the number of moving objects appearing in a front view image is so limited that it is hard to detect a test moving object, a predetermined number of moving time durations can be accumulated in order to calculate reaction time duration. Thus, a driver's alertness level can be detected.

The stimulus display is performed to stimulate a driver's visual sensation during when the vehicle 1 is in a stationary state. Thus, the stimulus display will not interrupt driving of the vehicle.

Figure 14:
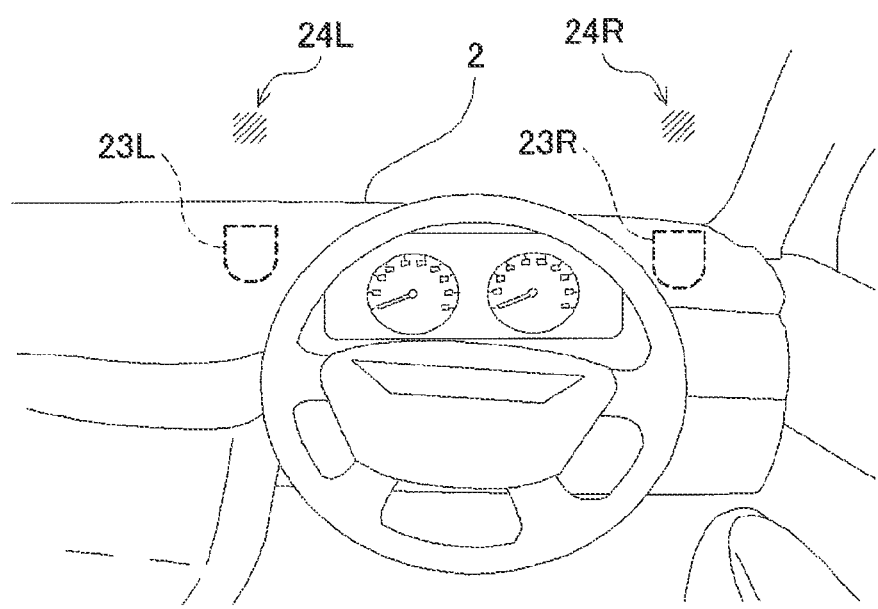
FIG. 14 is an explanatory diagram showing a situation in which stimulus images are projected onto windshield.

In the above-described third embodiment, the display device 22L or 22R placed on the dashboard 2 is turned on and performs a stimulus display to stimulate a driver's visual sensation. For another example, as shown in FIG. 14, projection display devices 23L and 23R may be embedded in the dashboard 2. The projection display devices 23L and 23R may be used to project or display small stimulus images 24L and 24R, which attract driver's attention. The projection display devices 23L and 23R project or display the stimulus images onto the windshield of the vehicle 1 for the purpose of performing stimulus display. A head-up display device may be used as the projection display devices 23L and 24R in order to display the stimulus images 24L and 24R.

In this way, the stimulus images 24L and 24R can be displayed at positions where the stimulus images can more readily catch the driver's eye than the display devices 22L and 22R can. Thus, an alertness level can be detected at a higher accuracy. Naturally, the stimulus images 24L and 24R are displayed when the vehicle 1 is in a stationary state. Thus, driving performed by the driver is avoided to be interrupted by the stimulus display.

In above-described alertness level detection apparatus and the alertness level detection method of the present disclosure, when a new stimulus to a driver's visual sensation occurs within the range of a driver's viewable range, a moving time duration to be taken for a driver's line of sight to move to the position where the stimulus has occurred is detected. A driver's alertness level is then determined based on the moving time durations.

When a new stimulus occurs to a driver's visual sensation, a driver reflectively moves his/her line of sight to the position of the stimulus. A moving time duration, which is taken until the line of sight moves to the stimulus after the occurrence of the stimulus, reflects the quickness in a driver's brain activity. Therefore, once moving time durations are detected, a driver's alertness level can be detected at a higher accuracy and a higher reliability according to a direct measurement of the driver's brain activity.

In the above-described alertness level detection apparatus of the present disclosure, a front view image is generated in a travel direction of a vehicle. By analyzing the front view image, the alertness level detection apparatus may acquire information (stimulus information) indicating the occurrence time point of a new stimulus to a driver's visual sensation and an appearance position of the stimulus object.

Usually, a driver carefully watches ahead during a driving of the vehicle. Thus, whether new stimulus is provided to a driver's visual sensation can be detected by analyzing a front view image.

The following will describe an acquirement of the stimulus information performed by the above-described alertness level detection apparatus of the present disclosure. First, the alertness level detection apparatus generates a front view image at regular intervals in order to detect moving objects included in the front view image. If a new moving object is detected in a front view image, the timing when the front view image has been generated, and a position in the front view image where the moving object has been detected may be acquired as stimulus information.

Usually, when a new moving object appears in traveling direction, a driver reflectively moves his/her line of sight to the moving object. When a new moving object is detected in one of the front view images generated at regular intervals, the driver presumably moves his/her line of sight to the moving object. Accordingly, once the timing when the front view image has been produced and a position in the front view image where the moving object has been detected are acquired, the image generation time information and the position information can be used as stimulus information.

In the above-described alertness level detection apparatus of the present disclosure, instead of analyzing a front view image, stimulus information may be acquired as described below. First, predetermined stimulus display is enabled to be made at a predetermined position designated within the range of a driver's viewable range. The timing and position at which the stimulus display has been made may be acquired as stimulus information.

In this case, in whatever ambient environment a vehicle is traveling, a driver's alertness level can be detected by detecting moving time durations taken for moving to the stimulus display.

In the above-described alertness level detection apparatus of the present disclosure that makes stimulus display, stimulus display may be performed by displaying a predetermined stimulus image to the driver.

Stimulus display functions as a stimulus to a driver's visual sensation. Therefore, stimulus display can be achieved in various forms, for example, by turning on a lamp. When an image that attracts driver's attention is designated as a stimulus image, when the stimulus image is displayed, a driver moves his/her line of sight without fail. Therefore, a moving speed can be detected with a higher accuracy. As a result, a driver's alertness level can be detected at a higher accuracy.

In the above-described alertness level detection apparatus of the present disclosure that performs stimulus display, the stationary state of the vehicle may be detected, and stimulus display may be performed when the vehicle is in the stationary state rather than a travelling state.

Above configuration can avoid a fear that driving may be interrupted by performing stimulus display.

In the above-described alertness level detection apparatus of the present disclosure, a predetermined number of moving time durations may be accumulated, and an alertness level may be detected based on the multiple records of the accumulated moving time durations.

In this case, even if moving time durations have a variance, an alertness level can be detected at a higher accuracy based on multiple records of moving time durations.

In the above-described alertness level detection apparatus of the present disclosure that detects an alertness level based on a predetermined number of moving time durations, every time multiple moving time durations are accumulated, a time duration indicating the multiple moving time durations may be determined as a reaction time duration. The obtained reaction time duration is compared with a predetermined reaction time duration (reference reaction time duration), which is determined in advance as a reference. If the reaction time duration obtained based on the multiple accumulated moving time durations is shorter, the reference reaction time duration is updated with the newly obtained reaction time duration.

While the reference reaction time duration is updated, every time a new reaction time duration is determined, an alertness level may be determined based on a deviation from the reference reaction time duration at that time.

In this way, a reaction time duration obtained when a driver's alertness level is highest is designated as a reference reaction time duration. Thereafter, as the driver's alertness level decreases, the reaction time duration increases to get larger than the reference reaction time duration. Since the alertness level is detected with a state, in which a specified driver is most alerted, as a reference, the alertness level can be detected highly precisely for the specified driver while being unaffected by an individual difference of other drivers.

While the disclosure has been described with reference to preferred embodiments thereof, it is to be understood that the disclosure is not limited to the preferred embodiments and constructions. The disclosure is intended to cover various modification and equivalent arrangements. In addition, while the various combinations and configurations, which are preferred, other combinations and configurations, including more, less or only a single element, are also within the spirit and scope of the disclosure.

The invention claimed is:

1. An alertness level detection apparatus equipped to a vehicle and detecting an alertness level of a driver, the alertness level detection apparatus comprising:
   a stimulus information acquirer detecting a stimulus newly applied to a visual sensation of the driver within a visual field of the driver under a state in which the driver watches in a travel direction of the vehicle and acquiring stimulus information related to an occurrence time of the stimulus and an occurrence position of the stimulus within the visual field of the driver;
   a face image generator generating a face image of the driver;
   a line-of-sight position detector detecting a position of a line of sight of the driver by analyzing the face image;
   a moving time duration detector detecting a moving time duration taken for the driver to move the line of sight to the occurrence position of the stimulus immediately after the occurrence time of the stimulus; and
   an alertness level determiner determining the alertness level of the driver based on the moving time duration.

2. The alertness level detection apparatus according to claim 1, further comprising
   a front view image generator equipped to the vehicle and generating a front view image taken in the travel direction of the vehicle,
   wherein the stimulus information acquirer acquires the stimulus information by analyzing the front view image.

3. The alertness level detection apparatus according to claim 2, wherein
   the front view image generator generates a plurality of the front view images at predetermined intervals, and
   when the stimulus information detects a moving object as the stimulus in one of the plurality of the front view images, the stimulus information acquirer acquires, as the stimulus information, a generation time of the one of the plurality of the front view images and a position of the moving object in the one of the plurality of the front view images.

4. The alertness level detection apparatus according to claim 1, further comprising
   a stimulus display unit performing a stimulus display, as the stimulus applied to the visual sensation of the driver, at a predetermined display position defined within the visual field of the driver,
   wherein the stimulus information acquirer acquires, as the stimulus information, an execution time of the stimulus display and the predetermined display position of the stimulus display.

5. The alertness level detection apparatus according to claim 4,
   wherein the stimulus display unit displays a predetermined stimulus image as the performing of the stimulus display.

6. The alertness level detection apparatus according to claim 4, further comprising
   a stationary state detector detecting a stationary state of the vehicle,
   wherein the stimulus display unit performs the stimulus display under a condition that the vehicle is in the stationary state.

7. The alertness level detection apparatus according to claim 1, further comprising
   an accumulator accumulating a predetermined number of the moving time durations,
   wherein the alertness level determiner determines the alertness level of the driver based on the predetermined number of the moving time durations.

8. The alertness level detection apparatus according to claim 7, wherein
   the alertness level determiner includes:
   a reaction time duration determiner determining a reaction time duration, which indicates the predetermined number of the moving time durations, based on the predetermined number of the moving time durations every time the predetermined number of the moving time durations are accumulated; and
   an updater comparing the reaction time duration determined by the reaction time duration determiner with a reference reaction time duration that is preliminarily set, wherein, when the reaction time duration is shorter than the reference reaction time duration, the updater updates the reference reaction time duration with the reaction time duration, and
   the alertness level determiner determines the alertness level of the driver based on a deviation of the reaction time duration from the reference reaction time duration.

9. An alertness level detection method applied to a vehicle for detecting an alertness level of a driver, the alertness level detection method comprising:
   detecting a stimulus newly applied to a visual sensation of a driver within a visual field of the driver under a state in which the driver watches in a travel direction of the vehicle;
   acquiring stimulus information related to an occurrence time of the stimulus and an occurrence position of the stimulus within the visual field of the driver;
   generating a face image of the driver;
   detecting a position of a line of sight of the driver by analyzing the face image;
   detecting a moving time duration taken for the driver to move the line of sight to the occurrence position of the stimulus immediately after the occurrence time of the stimulus; and
   determining the alertness level of the driver based on the moving time duration.

* * * * *